US010016526B2

(12) United States Patent
Shim (10) Patent No.: US 10,016,526 B2
(45) Date of Patent: Jul. 10, 2018

(54) PASTE-POWDER DUAL POLYMER-BASED BONE CEMENT AND INJECTION APPARATUS FOR SAME

(75) Inventor: Jae Bum Shim, Gyeonggi-do (KR)

(73) Assignee: INJECTA INC., Gyeonggi-Do (KR)

( * ) Notice: Subject to any disclaimer, the term of this patent is extended or adjusted under 35 U.S.C. 154(b) by 1241 days.

(21) Appl. No.: 13/142,338

(22) PCT Filed: Nov. 4, 2010

(86) PCT No.: PCT/KR2010/007774
§ 371 (c)(1),
(2), (4) Date: Jun. 27, 2011

(87) PCT Pub. No.: WO2011/056006
PCT Pub. Date: May 12, 2011

(65) Prior Publication Data
US 2011/0270259 A1    Nov. 3, 2011

(30) Foreign Application Priority Data

Nov. 6, 2009   (KR) .................. 10-2009-0106948
Nov. 1, 2010   (KR) .................. 10-2010-0107656

(51) Int. Cl.
| A61L 24/06 | (2006.01) |
| A61L 24/00 | (2006.01) |
| A61L 27/16 | (2006.01) |
| A61M 25/00 | (2006.01) |
| A61B 17/88 | (2006.01) |

(52) U.S. Cl.
CPC .......... *A61L 24/0015* (2013.01); *A61L 24/06* (2013.01); *A61L 27/16* (2013.01); *A61M 25/00* (2013.01); *A61B 17/8805* (2013.01); *A61L 2300/406* (2013.01); *A61L 2300/44* (2013.01); *A61L 2430/02* (2013.01)

(58) Field of Classification Search
CPC ...................................... A61L 24/06
USPC ....................................... 523/116
See application file for complete search history.

(56) References Cited

U.S. PATENT DOCUMENTS

| 4,490,497 | A |   | 12/1984 | Evrard et al. |
| 5,114,240 | A |   | 5/1992  | Kindt-Larsen et al. |
| 5,193,907 | A |   | 3/1993  | Faccioli et al. |
| 5,819,988 | A | * | 10/1998 | Sawhney et al. ............ 222/137 |
| 6,593,394 | B1 | * | 7/2003 | Li et al. ........................ 523/113 |
| 7,569,621 | B2 |  | 8/2009 | Klaus-Dieter et al. |
| 2006/0292199 | A1 | * | 12/2006 | Kuhn et al. ................... 424/422 |
| 2008/0039586 | A1 | * | 2/2008 | Hasenwinkel et al. ....... 525/192 |
| 2008/0044374 | A1 | * | 2/2008 | Lavergne et al. .......... 424/78.31 |
| 2009/0105366 | A1 | * | 4/2009 | Vogt et al. .................... 523/116 |
| 2009/0105367 | A1 | * | 4/2009 | Vogt ..................... A61L 24/001 523/116 |

FOREIGN PATENT DOCUMENTS

| EP | 1886648 A1 | 2/2008 |
| JP | 06-261932 A | 9/1994 |
| KR | 10-0957543 B1 | 5/2010 |
| WO | 2005/069837 A2 | 8/2005 |
| WO | 2007/133355 A2 | 11/2007 |
| WO | 2009/097152 A1 | 8/2009 |

OTHER PUBLICATIONS

International Search Report for PCT/KR2010/07774, dated Jul. 11, 2011.
Supplementary European Search Report Application No. EP 10828541.2 submitted herein, dated May 8, 2014.
Office action dated Sep. 10, 2013 from State Intellectual Property Office of the P.R.C (SIPO) in a counterpart Chinese patent application No. 201080054011.8.

* cited by examiner

*Primary Examiner* — Michael F Pepitone
(74) *Attorney, Agent, or Firm* — The PL Law Group, PLLC (57) ABSTRACT

The present invention relates to a paste-powder binary bone cement used in arthroplasty or vertebroplasty, and, more particularly, to a paste-powder binary bone cement which can be directly used at a site to be treated without additionally waiting it to the site by dissolving predetermined chemically-unreactive powdered compositions in a liquid monomer to form paste having high viscosity and then mixing other powdered components with the paste in a minimum amount of air, and to an apparatus for injecting the same.

10 Claims, 6 Drawing Sheets

PASTE-POWDER DUAL POLYMER-BASED BONE CEMENT AND INJECTION APPARATUS FOR SAME

This is a National Phase Application filed under 35 U.S.C. § 371 as a national stage of PCT/KR2010/007774, filed on Nov. 4, 2010, claiming the benefit from Korean Patent Application 10-2009-0106948, filed on Nov. 6, 2009, and claiming the benefit from Korean Patent Application 10-2010-0107656, filed on Nov. 1, 2010, the content of each of which is hereby incorporated by reference in its entirety.

TECHNICAL FIELD

The present invention relates to a paste-powder bone cement used in arthroplasty or vertebroplasty, and, more particularly, to a paste-powder binary polymer bone cement which can be directly used at a site to be treated without additionally waiting time it to the site by dissolving predetermined chemically-unreactive powdered components in a liquid monomer to form paste having high viscosity and then mixing other powdered components with the paste in a minimum amount of air, and to an apparatus for injecting the same.

BACKGROUND ART

Due to the damage of the vertebra or bone, various methods of embedding artificial material into the body have been used. Particularly, due to the damage of various kinds of joints, vertebrae and bones, the total joint arthroplasty and re-operation on knee joints or hip joints have been widely used. In this case, in order to replenish the bone loss associated with such arthroplasty and the operation, a bone cement is used to fix the artificial material embedded in the body.

Bone cements, each of which is a material for reinforcing fluidity, primarily serve to replenish the bone loss attributable to a bone fracture or a surgical operation or serve to transfer mechanical loading between an implant and bone by stabilizing the implant. Bone cements are broadly classified into polymer bone cements and ceramic bone cements. Here, a ceramic bone cement includes calcium phosphate (including apatite) and bioceramics having biocompatibility as main components, and is frequently used as an alternative to bone loss because it has excellent biocompatibility to tissues in the body. However, since a ceramic bone cement has low strength, a bone cement is generally used to fix an artificial material such as an implant instead of ceramic bone cement.

A bone cement includes a powder component and a liquid component. At the time of operation, these powder and liquid components are mixed with each other to form a paste, and then the paste is used. The powder component includes polymethyl methacrylate (PMMA) as a main composition, and, in a commercially-available bone cement, the powder component may include a copolymer of methacrylate and styrene as a main component. Further, the powder component includes benzoyl peroxide, which is a free-radical polymerization initiator. Further, the powder component includes barium sulfate or zirconium oxide, which is a radiopacifier, in order to enhance opacity to X-rays. Furthermore, the powder component includes gentamicin or the like as an antibiotic for preventing the infection of bacteria during an operation.

The liquid component includes methyl methacrylate, which is a monomer as a main component. Further, the liquid component may include N,N-dimethyl-p-toluidine (or dimethylaminophenyl ethanol). N,N-dimethyl-p-toluidine acts as a free-radical activator to accelerate the formation of free radicals. Furthermore, the liquid component includes a very small amount of hydroquinone as a stabilizer to inhibit a self polymerization reaction when storing the bone cement.

When the powder component and the liquid component are mixed with each other, the mixture's viscosity is rapidly increased in proportion to the dissolution rate of polymer powder in a liquid monomer under an initial state of high fluidity, and thus the mixture thereof is formed into a doughy mixture. At this time, exothermic radical polymerization starts. That is, the exothermic radical polymerization is performed by reacting benzoyl peroxide, which is a polymerization initiator included in the powder component, with methyl methacylate, which is included in the liquid component. In this case, the polymerization degree, strength, porosity and residual monomers of the bone cement are determined by the freedom degree and concentration of free electrons, which are caused by the initial viscosity. Such a doughy mixture is solidified by polymerization and serves to fix an artificial implant.

In a surgical procedure involving a bone cement, when a powder and a liquid components are mixed with each other to form a doughy mixture having a predetermined viscosity (at this time (dough time), the doughy mixture does not adhere to surgical gloves (powder-free latex gloves)), the surgical procedure thereof is performed at the time of clinical application, that is, at the time that the bone cement that easily adheres to the bone loss portion is injected into the human body. Therefore, the surgical procedure includes the steps of mixing, waiting, dough, and working. Further, the surgical procedure may further include the step of setting in which working is no longer able to be conducted because of the deterioration in the viscosity attributable to polymerization in the doughy bone cement. Mixing, waiting, working and setting are greatly influenced by the characteristics (for example, the bead size, molecular weight, swelling characteristics thereof to non-crosslinked MMA monomer) of the PMMA polymer and by the working temperature.

Therefore, the doughy bone cement best adhere to the portion where there is bone loss when the polymerization characteristics of the doughy bone cement and the injection timing thereof are synthetically determined. That is, when the doughy bone cement is applied to bone tissue, the free radical polymerization in the doughy bone cement rapidly accelerates while the surrounding temperature rises from room temperature to body temperature, so that the elasticity of the viscoelastic doughy bone cement increases, with the result that the diffusion of radicals and monomer molecules decreases, thereby rapidly reaching the setting time. Since operation is physically limited when the elasticity of the doughy bone cement rapidly increases, the viscoelastic doughy bone cement is applied to the periphery of bone tissue or hardens when the polymerization characteristics of the applied doughy bone cement are not accurately understood and the injection time of the doughy bone cement is decided excessively rapid or slow. Therefore, various mixing and dispensing apparatuses for minimizing the differences in the application of a bone cement attributable to the different clinical experiences of doctors are being actually developed.

Meanwhile, general powder-liquid bone cements are classified into the two categories of low-viscosity bone cements and high-viscosity bone cements, depending on the initial viscosity thereof. A low-viscosity bone cement, which has high initial fluidity, is advantageous in that it can be sufficiently prepared before work starts because the time it takes bone cement to form a doughy bone cement is long, but is problematic in that its operation time becomes long. A high-viscosity bone cement, which has low initial fluidity, is problematic in that it must be rapidly applied because it hardens rapidly. However, the high-viscosity bone cement is advantageous in that it does not mix with blood because it can endure the pressure of bleeding occurring at the periphery of the bone tissue treated with a bone cement, and in that it can be rapidly applied to the bone tissue. However, in the application of high-viscosity bone cement, a vacuum mixer for preventing the introduction of air, due to the high viscosity of a bone cement, during the mixing process and a high-pressure injector for injecting a high-viscosity bone cement must be additionally used. These vacuum mixer and high-pressure injector are gradually becoming diversified and complicated. Such a diversified and complicated mixer and injector function to reduce the clinical difference attributable to the complicated polymerization characteristics of a bone cement, but are problematic in that the time it takes to apply a bone cement is lengthened due to complicated mixing and injecting processes, and instruments necessary for each of the processes must be purchased, thus increasing medical expenses.

DISCLOSURE

Technical Problem

The present inventors made efforts to solve the above-mentioned problems. As a result, they developed a technology for forming a viscous paste by dissolving predetermined chemically-unreactive powdered components in a liquid monomer, thus culminating in the present invention.

Accordingly, an object of the present invention is to provide a paste-powder binary bone cement, which can be formed into a dough having viscosity that can be directly introduced into the body after mixing a paste component (Vs) and a powder component (Ps) and which can reduce the operating time because an waiting process is not required unlike a general powder-liquid bone cement that is formed into a dough through mixing and waiting processes, and an apparatus for injecting the same.

Another object of the present invention is to provide a paste-powder binary bone cement, which can minimize the personal technical difference of doctors that can occur in the mixing and applying process thereof because free radicals formed by a BPO-DMPT initiation reaction have low molecular diffusion around MMA molecules due to the high-viscosity polymer bone cement and thus the polymerization of MMA is initiated together with the injection of the doughy polymer bone cement into the body, and an apparatus for injecting the same.

Still another object of the present invention is to provide a paste-powder binary bone cement, which can be easily injected into the body in the form of a dough because it is formed into a dough having viscosity suitable for injection into the body and the exposure thereof to air and the mixing thereof with air during a mixing process are minimized, and an apparatus for injecting the same.

Still another object of the present invention is to provide a paste-powder binary bone cement, which can be rapidly applied because a vacuum mixer for preventing the exposure of the bone cement to air and a high-pressure injector for injecting the polymer bone cement into the body are not required and thus the preparation process required to perform an operation are not additionally required, and which can alleviate the economic burden of patients because it does not require additional instruments and can thus lead to the reduction in medical expenses, and an apparatus for injecting the same.

Objects of the present invention are not limited to the above-mentioned objects, and other objects of the present invention, not mentioned, will be clearly understood by those skilled in the art from the following descriptions.

Technical Solution

In order to accomplish the above objects, an aspect of the present invention provides a paste-powder binary bone cement, comprising: a paste component prepared by preliminarily dissolving a first powdered composition in a liquid component; and a powder component including a second powdered composition, wherein the paste component is mixed with the powder component to immediately form a doughy bone cement without dough time.

In the paste-powder binary bone cement, the total amount of the first powdered component included in 1 mL of the liquid component and the second powdered component is 1.5~2.5 g, the amount of the first powdered component is 25~80 wt % based on the total amount of the first powdered component and the second powdered component, and the amount of the second powdered component is 20~75 wt % based on the total amount of the first powdered component and the second powdered component.

Further, the first powdered component includes an acrylic polymer, a radiopaque agent and an antibiotic, the liquid component includes a non-crosslinked MMA monomer, a free radical activator, and the second powdered component includes an acrylic polymer, a free radical initiator and an antibiotic.

Further, the acrylic polymer is selected from the group consisting of a PMMA polymer (polymethylmethacrylate) which is a linear copolymer of non-crosslinked MMA monomers, polymethylacrylate, polystyrene, and copolymers thereof.

Further, the acrylic polymer is formed into a bead having a diamer of 10~100 μm.

Further, the acrylic polymer has a weight average molecular weight of 50,000~200,000.

Further, the free radical initiator is benzoyl peroxide, and the free radical activator is N,N-dimethyl-para-toluidine.

Further, the amount of the free radical initiator is 0.25~2.5 wt % based on the total amount of the first powdered component and the second powdered component, and the amount of the free radical activator is 0.5~2.5 vol % based on the volume of the liquid component.

Further, the radiopaque agent is barium sulfate ($BaSO_4$) or zirconium dioxide ($ZrO_2$), and the amount of the radiopaque agent is 10~30 wt % based on the total amount of the first powdered component and the second powdered component.

Further, the free radical inhibitor is hydroquinone, and is included in the liquid component in an amount of 0.01~150 ppm based on the volume of the liquid component.

Further, the amount of the antibiotic is 2.5 wt % or less based on the total amount of the first powdered component and the second powdered component.

Another aspect of the present invention provides an apparatus for injecting the paste-powder binary bone cement, comprising: a coaxial two-component cartridge including inner and outer cartridges; and a mixing tube connected to the coaxial two-component cartridge and provided therein with a mixing impeller.

In the apparatus, one side of the coaxial two-component cartridge is charged with the paste component, and the other side thereof is charged with the powder component.

Further, the inner cartridge of the coaxial two-component cartridge has a planar tubular shape, and is thus circularly surrounded by the outer cartridge.

Further, the coaxial two-component cartridge and the mixing tube can be detached from each other.

Advantageous Effects

The paste-powder binary bone cement and apparatus for injecting the same according to the present invention have the following effects.

First, according to the present invention, the paste-powder binary bone cement can be formed into a viscous dough that can be directly introduced into the body after mixing paste component (Vs) and powder component (Ps) and which can reduce the operating time because an waiting process is not required unlike general powder-liquid bone cement that is formed into a dough through mixing and waiting processes.

Further, according to the present invention, the paste-powder binary bone cement can minimize the personal technical difference of doctors that can occur in the mixing and applying process thereof because free radicals formed by a BPO-DMPT initiation reaction have low molecular mobility around MMA molecules due to the high-viscosity dough and thus the polymerization of MMA is initiated together with the injection of the bone cement into the body.

Further, according to the present invention, the paste-powder binary bone cement can be easily injected into the body in the form of a dough because it is formed into a dough having a viscosity suitable for injection into the body and the exposure thereof to air and the mixing thereof with air during a mixing process are minimized.

Further, according to the present invention, the paste-powder binary bone cement can be rapidly applied because a vacuum mixer for preventing the exposure of the polymer bone cement to air and a high-pressure injector for injecting the polymer bone cement into the body are not required and thus the preparation process necessary for performing an operation does not have additionally requirements, and can alleviate the economic burden of patients because it does not require additional instruments and can thus lead to a reduction in medical expenses.

BEST MODE

The terms and words used in the present specification and claims should not be interpreted as being limited to typical meanings or dictionary definitions, but should be interpreted as having meanings and concepts relevant to the technical scope of the present invention based on the rule according to which an inventor can appropriately define the concept of the term to describe the best method he or she knows for carrying out the invention.

Hereinafter, preferred embodiments of the present invention will be described in detail with reference to the attached drawings.

However, the present invention is not limited to the following embodiments, and may be variously modified. The same reference numerals are used throughout the accompanying drawings to designate the same or similar components, and redundant descriptions thereof are omitted.

The present invention provides a paste-powder binary bone cement, which can be formed into a viscous dough that can be directly introduced into the body after mixing a paste component (Vs) and a powder component (Ps), and which can reduce the operating time without performing an waiting process. As a result, the present invention can solve the problems occurring when a general powder-liquid bone cement is formed into a dough, that is, a paste through mixing and waiting processes.

Therefore, the paste-powder binary bone cement of the present invention includes: a paste component prepared by preliminarily dissolving a first powdered composition in a liquid component; and a powder component including a second powdered component, wherein the paste component is mixed with the powder component to immediately form a doughy polymer bone cement without waiting time.

Here, it is preferred that the total amount of the first powdered component included in 1 mL of the liquid component and the second powdered component be 1.5~2.5 g, the amount of the first powdered component be 25~80 wt % based on the total amount of the first powdered component and the second powdered component, and the amount of the second powder component be 20~75 wt % based on the total amount of the first powdered component and the second powdered component Further, it is preferred that the first powder component include an acrylic polymer, a radiopaque agent and an antibiotic, the liquid component include a non-crosslinked MMA monomer, a free radical activator and the second powdered component include an acrylic polymer, a free radical initiator and an antibiotic.

In this case, the acrylic polymer may be selected from the group consisting of a PMMA polymer (polymethylmethacrylate) which is a linear copolymer of non-crosslinked MMA monomers, polymethyl methacrylate, polystyrene, and copolymers thereof. The acrylic polymer is not limited because it preliminarily dissolves in the liquid component. The acrylic polymer may be formed into beads each having a diameter of 10~100 μm, preferably 20~50 μm, and more preferably 25 μm. When the diameter of a bead is 25 μm, the acrylic polymer exhibits such solubility that the most excellent dough viscosity can be obtained when the powder component is mixed with the paste component. The acrylic polymer may have a weight average molecular weight (Mw) of 50,000~200,000. In particular, when the weight average molecular weight (Mw) of the acrylic polymer is 100,000 g/mol, it is most suitable to preliminarily dissolve the acrylic polymer.

Further, commonly known free radical initiators, free radical activators, radiopaque agents, free radical inhibitors, and antibiotics may be used. In particular, it is preferred that benzoyl peroxide (BPO) be used as the free radical initiator, N,N-dimethyl-para-toluidine (DMPT) be used as the free radical activator, barium sulfate ($BaSO_4$) or zirconium dioxide ($ZrO_2$) be used as the radiopaque agent, hydroquinone (HQ) be used as the free radical inhibitor, and gentamicin (GM) be used as the antibiotic.

Particularly, the amount of the free radical initiator is 0.25~2.5 wt % based on the total amount of the first powdered component and the second powdered component, the amount of the free radical activator is 0.5~2.5 vol % based on the volume of the liquid component, the amount of the radiopaque agent is 10~30 wt % based on the total amount of the first powdered component and the second powdered component, the free radical inhibitor is included in the liquid component in an amount of 0.01~150 ppm based on the volume of the liquid component, and the amount of the antibiotic is 2.5 wt % or less based on the total amount of the first powdered component and the second powdered component. The radiopaque agent ($BaSO_4$, barium sulfate) and antibiotic (GM, gentamicin), which do not dissolve in the non-crosslinked MMA monomer, are uniformly mixed in the liquid component because they serve to weaken mechanical properties in a polymerized and set matrix. Therefore, the radiopaque agent and antibiotic serve to prevent a general powder-liquid bone cement from uniformly mixing and aggregating.

Here, the radiopaque agent is used for radiation imaging. Since the radiopaque agent does not chemically dissolve in the non-crosslinked MMA monomer, in order that the radiopague agent does not aggregate and that the radiopaque agent uniformly distributes in the paste component, it is preferred that the radiopaque agent be mixed and separated before the acrylic polymer of the first powdered component is dissolved in the liquid component to exhibit viscosity. For this reason, the antibiotic is mixed with the radiopaque agent. That is, since the preliminary mixing of the radiopaque agent and the antibiotic is conducted in a state in which the acrylic polymer of the first powdered component does not exist and thus the preliminary mixture thereof is formed into the liquid component, higher uniformity than that of a dough obtained by mixing conventional powder-liquid bone cement can be obtained.

Meanwhile, the uniform distribution of the antibiotic is very important in terms of the mechanical strength of bone cement because it influences the distribution of pores occurring after bone tissues dissolve. It is preferred that the antibiotic be used in the same amount in both the paste component and the powder component. The antibiotic included in the powder component can be easily diffused into peripheral tissues and bone while the powder component is introduced there into in the form of dough, compared to the antibiotic preliminary mixed in the paste component. The antibiotic preliminary mixed in the paste component stays in the polymerized matrix for a long period of time and simultaneously exhibits uniform antibiotic effects.

As such, in the liquid component, the free radical activator (N,N-dimethyl-para-toluidine) and the free radical inhibitor (HQ, hydroquinone) are previously mixed and dissolved in the non-crosslinked MMA monomer. The free radical inhibitor is exposed to heat and light during the storage period, and serves to prevent the spontaneous polymerization of non-crosslinked MMA monomers. Generally, the free radical inhibitor is included in the non-crosslinked MMA monomer in an amount of about 10~100 ppm.

Paste component having various powder/liquid (P/L) ratios can be prepared depending on the amount of the acrylic polymer of the first powdered composition dissolved in the liquid composition. It is preferred that the ratio of the first powdered component preliminarily dissolved in the paste component to the liquid composition be 0.5~1.5 g/ml. The P/L ratio thereof may be selected depending on the average molecular weight (Mw) of acrylic polymer beads and the swelling characteristics of the liquid composition to the non-crosslinked MMA monomer. For example, when the P/L ratio of the paste composition (Vs) is 1 g/mol, for a total amount of powder of 40 g, 20 g of powder belongs to the first powdered composition of the paste component (Vs), and 20 g of powder belongs to the second powdered composition of the powder component (Ps). 20 g of the first powdered composition is preliminarily dissolved in 20 mL of the liquid composition (MMA, DMPT, HQ) to form the paste component (Vs).

The second powdered component, as described above, includes an acrylic polymer, a free radical initiator and an antibiotic. The second powdered component may be prepared in such a way that powder compositions mixed in a ball mill for 5 hours which contains ceramic balls having a diameter of 10 mm and rotates at 2 Hz, in which the powder components are charged in the ball mill in an amount of 2.5 g per one ceramic ball. The acrylic polymer may be a PMMA polymer which can be formed into beads having an average diameter of 25 μm, the free radical initiator may be benzoyl peroxide which can be formed into beads having an average diameter of 20 μm, and the antibiotic may be gentamicin which can be formed into beads having an average diameter of 10 μm.

When the second powdered component formed in this way is mixed with the paste component (Vs), the free radical initiator included in the second powdered component and the free radical activator included in the paste component (Vs) are rapidly diffused to form free radicals.

Further, the present invention provides an apparatus for injecting the above-mentioned paste-powder binary bone cement. The apparatus for injecting the paste-powder binary bone cement includes: a coaxial two-component cartridge including inner and outer cartridges; and a mixing tube connected to the coaxial two-component cartridge and provided therein with a mixing impeller. Here, one side of the coaxial two-component cartridge may be charged with paste component (Vs), and the other side thereof may be charged with powder component (Ps). Particularly, the powder component (Ps) may be charged in the inner cartridge having low internal friction after ceramic balls are removed therefrom, and the paste component (Vs) may be charged in the outer cartridge after it is preliminarily mixed at 0.5 Hz.

Further, the coaxial two-component cartridge is configured such that the inner cartridge thereof has a planar tubular shape and is circularly surrounded by the outer cartridge thereof. Therefore, when this apparatus is mounted in a commonly-known extruding gun and then the extruding gun is operated, the powder component (Ps) and the paste composition (Vs) are simultaneously extruded from the coaxial two-component cartridge, and are then mixed by the mixing impeller provided in the mixing tube and simultaneously injected into the body.

That is, the apparatus for injecting the paste-powder binary bone cement according to the present invention is configured such that the tubular inner cartridge is located in the center of the outer cartridge having a larger diameter and thus the compounds charged in the inner and outer cartridges are simultaneously extruded by the extruding gun. Thus, these two-component compounds can be extruded at various volume ratios by adjusting the volume of the inner cartridge.

As such, in this apparatus, since the mixing tube connected to the coaxial two-component cartridge is provided therein with the mixing impeller, the paste component (Vs) having viscosity and the powder component (Ps) can be continuously injected into the bone tissue or bone loss portion of a patient in the form of a dough using the mixing tube in which the bone cements (Vs and Ps) are mixed with each other while making a contact with a minimum of air thanks to the mixing impeller.

Meanwhile, if necessary, a mixing drum may be used in addition to the outer cartridge of the coaxial two-component cartridge to form a large amount of paste composition (Vs) and then to introduce a predetermined amount of the paste composition (Vs) into the outer cartridge in a vacuum. Further, when the volume of the outer cartridge of the coaxial two-component cartridge is 50 mL or less, a double-type injector having a volume of 50 cc, which has been conventionally used for epoxy adhesive, may also be used.

Further, since the apparatus for injecting the paste-powder binary bone cement according to the present invention is configured such that the coaxial two-component cartridge and the mixing tube can be detached from each other, a plurality of body parts can be operated on by another mixing tube including a mixing impeller. That is, after a predetermined body part has been operated on, the mixing tube is detached from the coaxial two-component cartridge, and then the coaxial two-component cartridge is sealed. In this case, when there are additional operations to perform, a new mixing tube is attached to the coaxial two-component cartridge and then used.

In the present invention, the polymerization reaction in the doughy polymer bone cement introduced into the body can be controlled in consideration of the concentration of free radicals (for example, BPO-DMPT) depending on the viscosity of the doughy bone cement and the clinical working time. In particular, the viscosity of the doughy bone cement was synthetically determined by measuring the average molecular weight (Mw) of the acrylic polymer included in the paste component (Vs) and measuring the viscosity of the paste component (Vs) depending on the swelling characteristics of the acrylic polymer to the non-crosslinked MMA monomer.

Further, in the present invention, as described later, the final dough viscosity of the paste-powder bone cement was measured by comparing the dough viscosity of the conventional powder-liquid bone cement with the viscosity of the paste component (Vs) at various P/L ratios. Further, the polymerization characteristics and mechanical properties of the paste-powder binary bone cement, such as the exothermic temperature, solidification time, MMA polymerization degree, compressive strength and bending strength, under various temperature conditions were examined using an exothermic testing method, a differential scanning calorimeter (DSC) and a universal mechanical tester based on ASTM (American Society for Testing and Materials) F451 and ISO (International Organization of Standardization) 5833.

MODE FOR INVENTION

Example 1

Paste component (Vs) 1 was obtained by preliminarily mixing 4 g of barium sulfate ($BaSO_4$), 0.5 g of gentamicin (GM) and 5.5 g of PMMA, each of which is a first powdered component, with 19.8 mL of non-crosslinked MMA monomer (including hydroquinone (HQ) as a free radical inhibitor) and 0.178 mL of DMPT, each of which is a liquid component, and then statically mixing a PMMA polymer as a first powdered component with the preliminary mixture in a ball mill which rotates at 0.5 Hz. In this case, when the process of forming the paste component (Vs) is conducted in an outer cartridge, it is preferred that air bubbles that can collect during the mixing process for 24 hours be removed from the outer cartridge by keeping the outer cartridge in cold storage at 4° C. for 5 hours after the mixing process has completed.

powder component (Ps) 1 was prepared by uniformly mixing a powdered mixture including 29 g of a PMMA polymer, 0.5 g of EPO and 0.5 g of GM, each of which is a second powdered component, with ceramic balls each having a diameter of 10 mm (one ceramic ball per 2.5 g of the powdered mixture) using a 500 mL teflon bottle for 5 hours in a ball mill at a rotation speed of 2 Hz.

Here, since the total amount of the first powdered component and the second powdered component is 40 g and the volume of the liquid component is 20 mL, the ratio of the paste composition (Vs) to the solid composition (Ps) (P/L ratio) was 0.5 g/mL.

Examples 2 to 11

Paste components (Vs) 2 to 11 and powder components (Ps) 2 to 11 were prepared in the same manner as Example 1, except that the amounts of PMMA polymers respectively included in the paste and powder components are different as shown in Table 1 below. The ratios of the paste components (Vs) to the powder components (P/L ratio) are shown in Table 1 below.

TABLE 1

| | | | Paste (Vs) | | | | | Solid (Ps) | | |
|---|---|---|---|---|---|---|---|---|---|---|
| | P/L ratio | | First powdered component (g) | | | Liquid component (Ml) | | Second powdered component (g) | | |
| Class. | (g/mol) | | PMMA | BaSO₄ | GM | MMA | DMPT | | PMMA | BPO | GM |
| Ex. 2 | 0.6 | Paste (Vs)2 | 7.5 | 4 | 0.5 | 19.8 | 0.178 | Solid (Ps)2 | 27 | 0.5 | 0.5 |
| Ex. 3 | 0.7 | Paste (Vs)3 | 9.5 | 4 | 0.5 | 19.8 | 0.178 | Solid (Ps)3 | 25 | 0.5 | 0.5 |
| Ex. 4 | 0.8 | Paste (Vs)4 | 11.5 | 4 | 0.5 | 19.8 | 0.178 | Solid (Ps)4 | 23 | 0.5 | 0.5 |
| Ex. 5 | 0.9 | Paste (Vs)5 | 13.5 | 4 | 0.5 | 19.8 | 0.178 | Solid (Ps)5 | 21 | 0.5 | 0.5 |
| Ex. 6 | 1.0 | Paste (Vs)6 | 15.5 | 4 | 0.5 | 19.8 | 0.178 | Solid (Ps)6 | 19 | 0.5 | 0.5 |
| Ex. 7 | 1.1 | Paste (Vs)7 | 17.5 | 4 | 0.5 | 19.8 | 0.178 | Solid (Ps)7 | 17 | 0.5 | 0.5 |
| Ex. 8 | 1.2 | Paste (Vs)8 | 19.5 | 4 | 0.5 | 19.8 | 0.178 | Solid (Ps)8 | 15 | 0.5 | 0.5 |
| Ex. 9 | 1.3 | Paste (Vs)9 | 21.5 | 4 | 0.5 | 19.8 | 0.178 | Solid (Ps)9 | 13 | 0.5 | 0.5 |
| Ex. 10 | 1.4 | Paste (Vs)10 | 23.5 | 4 | 0.5 | 19.8 | 0.178 | Solid (Ps)10 | 11 | 0.5 | 0.5 |
| Ex. 11 | 1.5 | Paste (Vs)11 | 25.5 | 4 | 0.5 | 19.8 | 0.178 | Solid (Ps)11 | 9 | 0.5 | 0.5 |

Experimental Example 1

Figure 1:
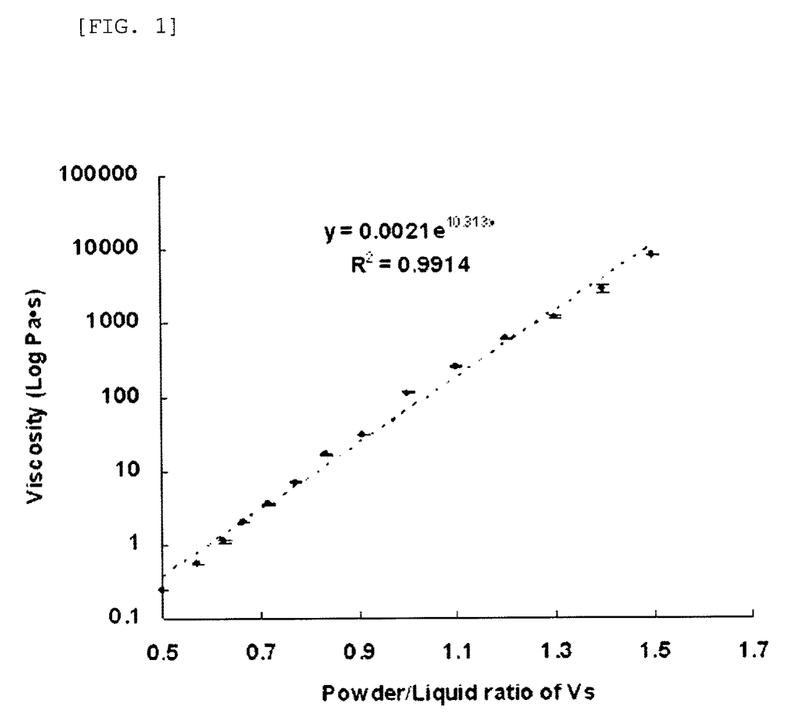
FIG. 1 is a graph showing the viscosity (log (Pa·s)) of paste component (Vs) having various P/L (powder/liquid) ratios (g/ml) according to embodiments of the present invention.

The viscosity of each of the paste components (Vs) 2 to 11 obtained from Examples 1 to 11 was measured depending on various P/L ratios, and the results thereof are shown in FIG. 1.

As shown in FIG. 1, it can be seen that the viscosity of the paste components (Vs) depending on the P/L ratio increases geometrically according to the concentration of a PMMA polymer. The reason for this is because the change in the viscosity of the paste components (Vs) depending on the P/L ratio attributable to the average molecular weight (Mw) of the PMMA polymer or the swelling characteristics of the PMMA polymer to the non-crosslinked MMA monomer is influenced by the vitrification of dissolved PMMA-MMA.

That is, the viscosity of the paste components (Vs) was 500 Pa·s at 23° C., and this viscosity was obtained at a P/L ratio of 0.7~1.5 g/mL. When the P/L ratio is increased within this range, the viscosity of the paste components (Vs) increases, and the amount of the powder components (Ps) correspondingly decreases, so that the final dough viscosity of the paste components (Vs) and the powder components (Ps) are limited to a range of 1000~2000 Pa·s within three minutes after the initiation of mixing.

As described in the following Experimental Example 2, it can be seen that the dough viscosity of the paste component (Vs) and the powder component (Ps) at 23° C. is about 1500 Pa·s at a P/L ratio of 0.8~1.0 g/ml, and that this doughy bone cement formed by mixing the paste component (Vs) with the powder component (Ps) is easily detached from the surface of a surgical powder-free latex glove.

Experimental Example 2

The volume ratio of the outer cartridge and the inner cartridge [paste component (Vs) and powder component (Ps)] was adjusted using the inner cartridge order-fabricated in consideration of the density (g/mL) of the powder component (Ps) for the various P/L ratios of the paste components (Vs) 1 to 11 obtained from Examples 1 to 11. The inner cartridge charged with the powder component (Ps) was connected with the outer cartridge charged with the viscous paste component (Vs), and was then mounted in the apparatus for injecting a paste-powder binary bone cement according to the present invention. The paste component (Vs) surrounding the powder component (Ps) was statically mixed by the mixing impeller without being brought into contact with air and without air being collected, to form a doughy bone cement.

About 40 mL of the doughy bone cement was charged in a 100 mL conical tube, and the viscosity of the doughy bone cement was measured using a spindle viscometer (RVDV-II, Brookfield, Mass., U.S.A.) at a spindle speed of 0.5 rpm. When the P/L ratio of the paste component (Vs) is in the range of 0.8~1.0 g/ml (that is, paste component (Vs) 4 to 6), the average viscosity of the doughy bone cement was 1500 Pa·s at 23° C. within three minutes after the initiation of mixing. In this case, the doughy bone cement effectively penetrates into cancellous bone tissue to obtain the structural stability with peripheral tissue at the time of final setting, and it is possible to prevent bleeding from occurring at the location of the operation.

Experimental Example 3

Figure 2:
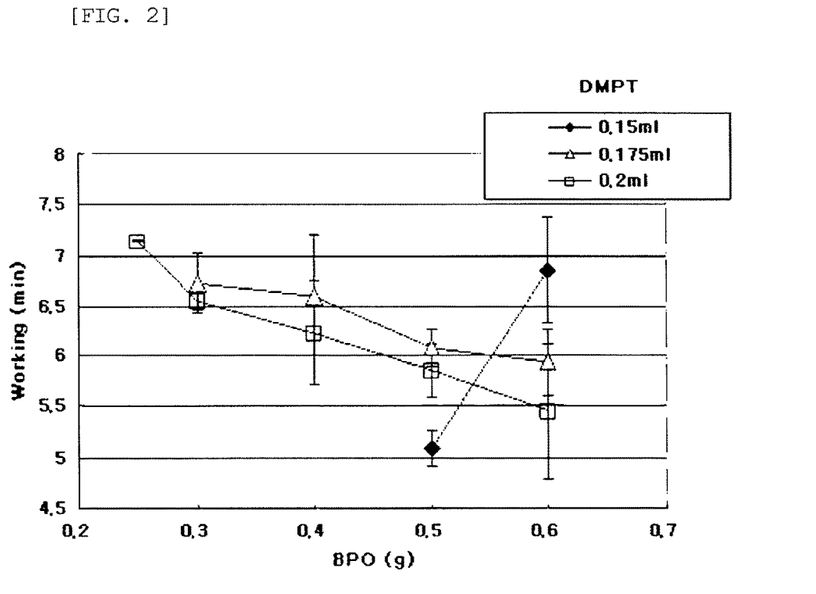
FIG. 2 is a graph showing the change in working time depending on the amount of BPO(g) and DMPT(ml) in the paste component (Vs) having a P/L ratio of 0.9 g/ml according to embodiments of the present invention.

Paste components (Vs) and powder components (Ps) were prepared in the same manner as Example 1 such that the concentrations of a free radical initiator (BPO) and a free radical activator (DMPT) were variously changed when the P/L ratio of the paste component (Vs) was 0.9 g/ml as shown in Table 1 above, and the effects of the concentration of BPO-DMPT on the polymerization reaction in the doughy polymer bone cement depending on various P/L ratios were examined using a differential scanning calorimeter (Diamond DSC, Perkin Elmer, Mass., U.S.A.) under an isothermal condition, and the results thereof are shown in FIG. 2. Further, due to the examination, the conversion rate of the polymerization reaction in the doughy bone cement under the conditions of an operating room temperature of 18.3~23° C. and a body temperature of 37.5° C. was indirectly analyzed. That is, when the mass of a sample is multiplied by the MMA concentration ratio (mass fraction) of a sample, the exothermic change of the differential scanning calorimeter (DSC) is obtained. The area of the exothermic change and the time designates a total calorie, and the conversion rate in the polymerization reaction, that is, the polymerization rate of non-crosslinked monomers, can be analyzed. The peak of the conversion rate was calculated by setting time that is the sum of mixing time and peak time, and the working time was calculated by the difference between the exothermic onset time of the differential scanning calorimeter (DSC) and the peak time.

It is known that the working time of a conventional powder-liquid bone cement containing a free radical activator (DMPT) at a relatively high concentration (for example, Surgical Simplex P, Howmedica, Ireland and CMW3G, Depuy, Eangland) is about 5.5~6.5 minutes after being mixed and adhered for 2~4 minutes at 65° F. (18.3° C.).

Figure 3:
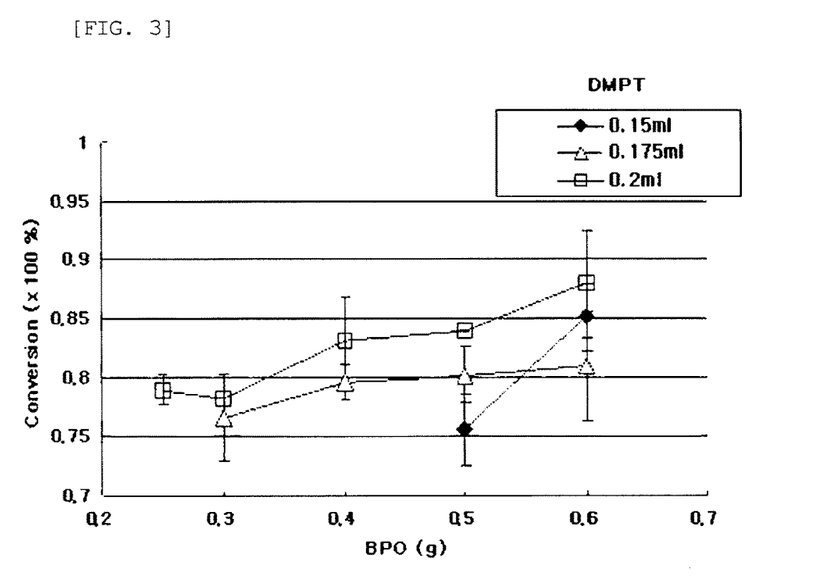
FIG. 3 is a graph showing the change in polymerization degree of MMA depending on the amount of BPO(g) and DMPT(ml) in the paste component (Vs) having a P/L ratio of 0.9 g/ml according to embodiments of the present invention.

As shown in FIGS. 2 and 3, in the paste-powder binary bone cement of the present invention, when a sample containing a free radical initiator (BPO) and a free radical activator (DMPT) at a low concentration was used, the polymerization reaction proceeded rapidly as the P/L ratio was increased. The working time of a sample containing 0.15 mL of a free radical activator (DMPT) and having a P/L ratio of 0.9 g/ml was 5~7 minutes depending on the concentration of a free radical initiator (BPO), which was similar to that of conventional powder-liquid bone cement. Further, the working time of a sample containing 0.175 mL of a free radical activator (DMPT) and having a P/L ratio of 0.9 g/ml was 6~7 minutes depending on the concentration of a free radical initiator (BPO), and, at this time, the conversion rate of the sample was maintained at about 80%, thus exhibiting the stability of polymerization. The conversion rate of the bone cement having a P/L ratio of 0.9 g/ml increased in proportion to the concentration of the free radical initiator (BPO) included in the powder component (Ps), and the working time thereof was decreased depending on the concentration thereof. However, in the sample containing 0.15 mL of a free radical activator (DMPT), the working time thereof increased even when the concentration of the free radical initiator (BPO) was increased.

The polymerization reaction in the doughy bone cement is greatly influenced by the surrounding temperature of various polymerizing environments. That is, at a high surrounding temperature, the activation energy of molecules is increased to decrease the viscosity of the doughy bone cement, and the diffusion of molecules is increased to accelerate the polymerization reaction in the doughy bone cement. Particularly, in the case of bone cement having high thermal sensitivity that is the most important factor in bone cement operation, since this polymer bone cement is rapidly set when it is introduced into the body (37.5° C.) at room temperature (23° C.), the working time is decreased.

Experimental Example 4

The setting times and MMA conversion rates of conventional powder-liquid bone cements, as control groups, (Simplex P: total amount of powder 40 g, volume of liquid component 20 mL, BPO 0.6 g, and DMPT 0.512 mL; and CMW3G: total amount of powder 40 g, volume of liquid component 19 mL, BPO 0.8 g, DMPT 0.48 mL) and the paste-powder binary bone cement of the present invention (INJ 1: P/L ratio 0.8 g/ml, BPO 0.5 g, and DMPT 0.178 mL) at iso-temperature were examined in the same manner as Experimental Example 3, and the results thereof are shown in FIGS. 4 and 5.

Figure 4:
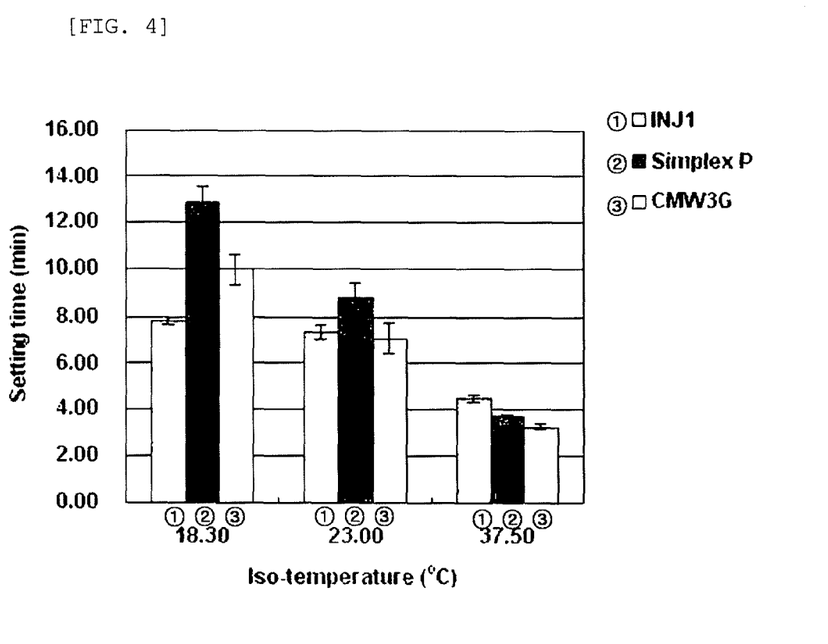
FIG. 4 is a graph showing the setting times of conventional power-liquid bone cements as control groups and the paste-powder binary bone cement manufactured by Example 4 of the present invention depending on iso-temperature.

As shown in FIG. 4, the thermal sensitivity of each of the conventional powder-liquid bone cements (for example, Surgical Simplex P, Howmedica, Ireland; and CMW3G, Depuy, England) relative to the surrounding temperature was higher than that of the paste-powder binary bone cement that is converted into dough without an waiting process. Therefore, the total setting time of each of the conventional powder-liquid bone cements was rapidly decreased as the surrounding temperature was increased.

Figure 5:
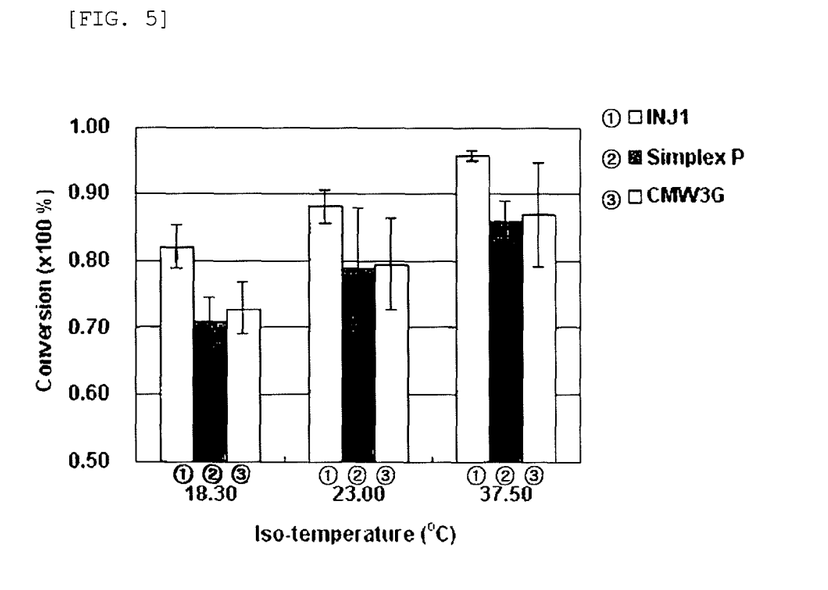
FIG. 5 is a graph showing the polymerization degrees of MMA of conventional power-liquid bone cements as control groups and the paste-powder binary bone cement manufactured by Example 4 of the present invention depending on iso-temperature.

Further, as shown in FIG. 5, the conversion rate of the paste-powder binary bone cement of the present invention (INJ1) was higher than that of each of the conventional powder-liquid bone cements. Therefore, it was ascertained that the thermal sensitivity of the paste-powder binary bone cement of the present invention is lower than that of the conventional powder-liquid bone cement, but the conversion rate thereof is higher than that of the conventional powder-liquid bone cement.

Experimental Example 5

The mechanical properties (compression and bending) and setting characteristics (setting time and maximum exothermic temperature) of the paste-powder binary bone cements of the present invention were evaluated and compared with those of conventional powder-liquid bone cements based on the test standards of ASTM F451 and ISO 5833. In this case, sample 1 is the same as that of Example 4, sample 2 is the same as sample 1 except that the amount of BPO is 0.6 g, and sample 3 is the same as sample 2 except that PMMA polymer beads having an average molecular weight of 100,000 g/mol and an average diameter of 50 μm are used and DMPT is used in an amount of 0.3 mL. The conventional powder-liquid bone cements (for example, Surgical Simplex P, Howmedica, Ireland; and CMW3G, Depuy, England) were mixed with each other by the mixing method and mixing temperature used in the manufacturing company thereof to form a doughy mixture. The doughy mixture was put into a Teflon mold for setting test, a compressive cylindrical mold (6 mm×12 mm: diameter and height) and a flexural square mold (75 mm×10 mm×3.3 mm), and the exothermic temperatures thereof were measured to obtain compressive and flexural strengths of the samples.

Figure 6:
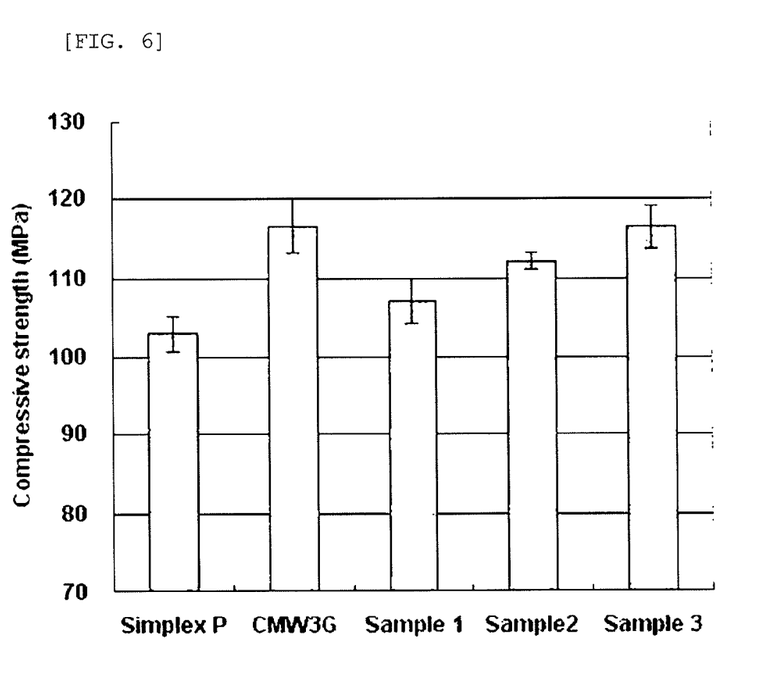
FIG. 6 is a graph showing the compressive strengths of conventional power-liquid bone cement and the paste-powder binary bone cement of the present invention.
Figure 7:
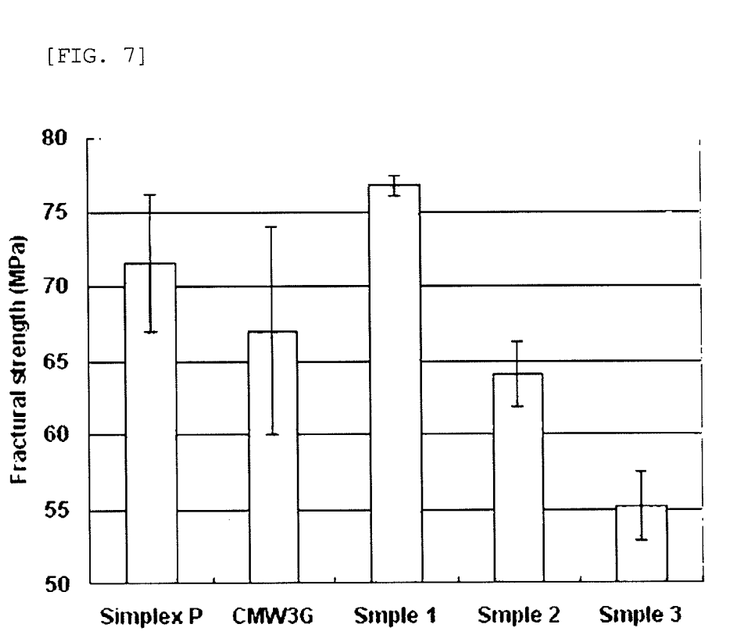
FIG. 7 is a graph showing the flexural bending strengths of conventional power-liquid bone cement and the paste-powder binary bone cement of the present invention.

As shown in FIGS. 6 and 7, the compressive strength of sample 3 containing PMMA polymer beads having a diameter of 50 μm was relatively high compared to other experimental groups (sample 1 and sample 2) and control groups (for example, Surgical Simplex P, Howmedica, Ireland; and CMW3G, Depuy, England), but the flexural strength thereof was relative low compared to the experimental groups and control groups. Sample 1 containing 0.5 g of a free radical initiator (EPO) exhibited high flexural strength compared to compressive strength. Further, all of the experimental groups (samples 1, 2 and 3) exhibited low maximum exothermic temperatures compared to the control groups, that is, powder-liquid bone cements (for example, Surgical Simplex P, Howmedica, Ireland; and CMW3G, Depuy, England). The reason for this is because the conversion of the paste-powder binary bone cement of the present invention into dough is immediately initiated and thus the exothermic temperature thereof is slowly increased compared to those of the control groups.

Experimental Example 6

The shelf-life of the self polymerization reaction of non-crosslinked MMA monomers, occurring when paste component is exposed to heat or light, was analyzed, and the effects of a free radical inhibitor (hydroquinone (HQ)) were evaluated. Paste compositions (Vs) were prepared in the same manner as Example 1, except that free radical inhibitors (HQ) (0, 50, 100 and 150 ppm), P/L ratio of paste (Vs) (0.8, 0.9, 1.0 and 1.2 g/ml), 0.5 mL of a free radical activator (DMPT), 4 g of a radiopaque agent (BaSO$_4$) and 0.5 g of an antibiotic (gentamicin (GM)) were used. The prepared paste component (Vs) were kept at 50, 55 and 60° C., respectively, and the change in viscosity thereof was measured every 24 hours in the same manner as Experimental Example 1. Further, the exothermic change of the self polymerization reaction of non-crosslinked MMA monomers was measured using a differential scanning calorimeter (DSC) at an isothermal temperature (T) of 80, 90 and 100° C., and exothermic initiation time ($t_o$) was analyzed using the Arrhenius Equation ($1/t_o$=A*exp[−Q/RT]). In the Arrhenius Equation, A is a pre-exponential factor, Q(J/mol) is activation energy, R(8.31 J/mol·K) is an ideal universal gas constant, and T(K) is an absolute temperature. The exothermic initiation time ($t_o$) at the target temperature (for example, room temperature) was predicted by analyzing the curve obtained by substituting the isothermal temperature (T) of 80, 90 and 100° C. and the measured exothermic initiation time ($t_o$) into the Arrhenius Equation and by analyzing the pre-exponential factor (A) and the activation energy (Q).

The change in viscosity of the paste component (Vs) increased geometrically under the isothermal temperature of 50, 55 and 60° C. However, the ability of the free radical inhibitor (HQ) added to the paste (Vs) to prevent the self-polymerization reaction of non-crosslinked MMA monomers was not effective in the statistics.

Figure 8:
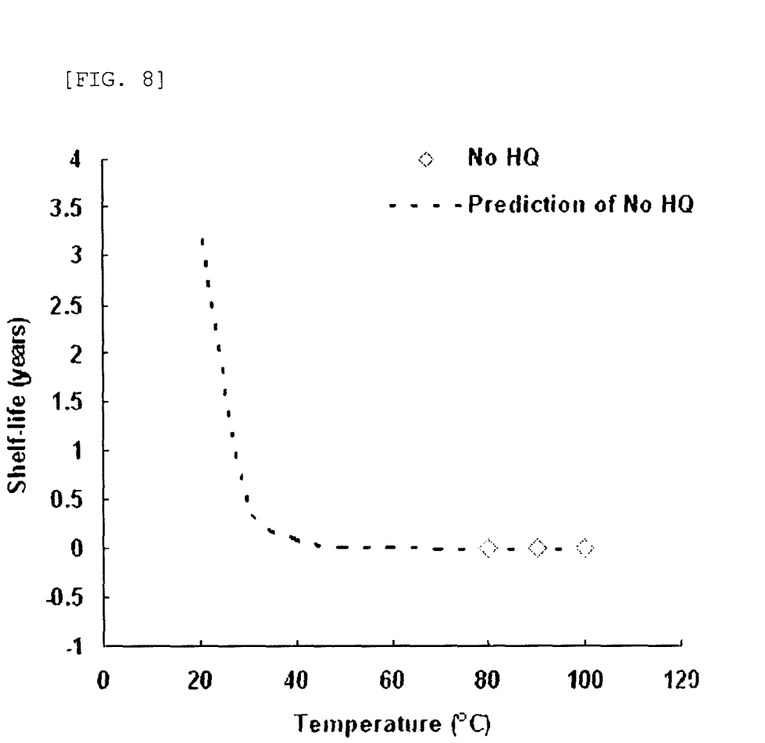
FIG. 8 is a graph showing the shelf life of paste components (Vs) at the target temperature in the paste-powder binary bone cement of the present invention, which was obtained by Arrhenius analysis after testing the self-polymerization of paste-type non-crosslinked MMM monomers using a differential scanning calorimeter (DSC).

As shown in FIG. 8, the shelf-life of the paste component (Vs) having a P/L ratio of 1 g/mL and containing 0.5 mL of a free radical activator (DMPT), predicted by the Arrhenius Equation ($1/t_o$=(1.09*1025)*exp[−17246/T]) using a differential scanning calorimeter (DSC) at 20° C. without adding the free radical inhibitor (HQ), was about 3.3 years, which was longer than the average shelf-life of conventional powder-liquid bone cements. For this reason, it was determined that the suitable shelf-life of the paste composition (Vs) can be secured without the free radical inhibitor (HQ).

However, in the Arrhenius analysis experiment using a differential scanning calorimeter (DSC), unlike the experiment conducted to determine the viscosity under an isothermal temperature of 50, 55 and it was evaluated that the analysis of the shelf-life of the sample containing a free radical inhibitor (HQ) at a concentration of 50 ppm was most effective at the target temperature (room temperature).

As described above, according to the paste-powder binary bone cement of the present invention, the preliminary mixing of a first powdered composition and a liquid composition to form paste component can be directly conducted using the outer cartridge of a coaxial two-component cartridge. However, when a large amount of the paste component is formed, a mixing drum may also be used, and thus a predetermined amount of the first powdered composition and the liquid composition can be charged into the cartridge in a vacuum. Therefore, the injection of the paste composition as well as the preliminary mixing thereof may also be conducted in a vacuum.

Further, according to the apparatus for injecting the paste-powder binary bone cement of the present invention, in order to reduce the friction between powder component (Ps) and the outlet of a cartridge at the time the powder component (Ps) is extruded, a coaxial two-component cartridge may be configured such that the inner cartridge thereof is surrounded by the outer cartridge thereof, thereby easily extruding the powder component (Ps). In this case, since the inner cartridge charged with viscous paste component (Vs) is surrounded by the outer cartridge charged with the powder component (Ps), the paste component (Vs) and the powder component (Ps) can be easily mixed by a mixing impeller provided in a mixing tube. However, when the total amount of the paste component (Vs) and the powder component (Ps) is less than 50 mL (in the present invention, the total amount thereof is 60 mL), a 50 cc dual syringe for epoxy adhesive may be used.

If possible, a small amount of the paste component (Vs) and the powder component (Ps) extruded from the cartridge by a mixing ball can be manually mixed using a spatula without using the mixing tube. Therefore, the paste-powder polymer bone cement of the present invention can be operated using the mixing ball instead of the mixing tube in small quantities.

Further, since the apparatus for injecting the paste-powder binary bone cement according to the present invention is configured such that the coaxial two-component cartridge and the mixing tube can be detached from each other, a plurality of parts can be operated using another mixing tube including a mixing impeller. That is, after a predetermined body part has been operated on, the mixing tube is detached from the coaxial two-component cartridge, and then the coaxial two-component cartridge is sealed. In this case, in order to perform additional operations, a new mixing tube is attached to the coaxial two-component cartridge and then used.

Meanwhile, although not specifically disclosed, when the paste-powder binary bone cement of the present invention is configured such that a paste component includes all preliminarily dissolved powder other than free radical initiator (BPO) and a powder component includes a very small amount of a free radical initiator (BPO), the paste component having suitable viscosity can be obtained using a PMMA polymer.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A paste-powder binary bone cement, consisting of:
   a paste component prepared by preliminarily dissolving a first powdered component in a liquid component, wherein the first powdered component consists of an acrylic polymer, a radiopaque agent and an antibiotic, the liquid component consists of a non-crosslinked MMA monomer, a free radical activator and a free radical inhibitor; and
   a powder component consisting of a second powdered component, wherein the second powdered component consists of an acrylic polymer, a free radical initiator and an antibiotic.

2. The paste-powder binary bone cement according to claim 1, wherein the total amount of the first powdered component included in 1 mL of the liquid component and the second powdered component is 1.5 to 2.5 g, the amount of the first powdered component is 25 to 80 wt % based on the total amount of the first powdered component and the second powdered component, and the amount of the second powdered component is 20~75 wt % based on the total amount of the first powdered component and the second powdered component.

3. The paste-powder binary bone cement according to claim 1, wherein the acrylic polymer is selected from the group consisting of a PMMA polymer (polymethyl methacrylate) which is a linear copolymer of non-crosslinked MMA monomers, polymethyl methacrylate, polystyrene, and copolymers thereof.

4. The paste-powder binary bone cement according to claim 1, wherein the acrylic polymer is formed into a bead having a diameter of 10~100 μm.

5. The paste-powder binary bone cement according to claim 1, wherein the acrylic polymer has a weight average molecular weight of 50,000~200,000.

6. The paste-powder polymer bone cement according to claim 1, wherein the free radical initiator is benzoyl peroxide, and the free radical activator is N,N-dimethyl-para-toluidine.

7. The paste-powder binary bone cement according to claim 1, wherein the amount of the free radical initiator is 0.25~2.5 wt % based on the total amount of the first powdered component and the second powdered component, and the amount of the free radical activator is 0.5~2.5 vol % based on the volume of the liquid component.

8. The paste-powder binary polymer bone cement according to claim 1, wherein the radiopaque agent is barium sulfate ($BaSO_4$) or zirconium dioxide ($ZrO_2$), and the amount of the radiopaque agent is 10~30 wt % based on the total amount of the first powdered component and the second powdered component.

9. The paste-powder binary bone cement according to claim 1, wherein the free radical inhibitor is hydroquinone, and is included in the liquid component in an amount of 0.01~150 ppm based on the volume of the liquid component.

10. The paste-powder binary bone cement according to claim 1, wherein the amount of the antibiotic is 2.5 wt % or less based on the total amount of the first powdered component and the second powdered component.

* * * * *